United States Patent
Orr

(10) Patent No.: US 9,839,754 B2
(45) Date of Patent: Dec. 12, 2017

(54) SYSTEM FOR PROVIDING SUPPORT THERAPY WHILE DETERMINING CONCENTRATIONS OF A MOLECULAR GASEOUS EXPIRED BY A SUBJECT RECEIVING PRESSURE SUPPORT THERAPY

(75) Inventor: Joseph Allen Orr, Park City, UT (US)

(73) Assignee: Koninklijke Philips N.V., Eindhoven (NL)

( * ) Notice: Subject to any disclaimer, the term of this patent is extended or adjusted under 35 U.S.C. 154(b) by 694 days.

(21) Appl. No.: 13/513,430

(22) PCT Filed: Nov. 23, 2010

(86) PCT No.: PCT/IB2010/055383
§ 371 (c)(1),
(2), (4) Date: Jun. 1, 2012

(87) PCT Pub. No.: WO2011/070472
PCT Pub. Date: Jun. 16, 2011

(65) Prior Publication Data
US 2012/0234324 A1 Sep. 20, 2012

Related U.S. Application Data

(60) Provisional application No. 61/267,282, filed on Dec. 7, 2009.

(51) Int. Cl.
*A61M 16/00* (2006.01)
*A61B 5/08* (2006.01)

(52) U.S. Cl.
CPC ........... *A61M 16/00* (2013.01); *A61B 5/082* (2013.01); *A61M 2016/0015* (2013.01);
(Continued)

(58) Field of Classification Search
CPC .... A61M 16/00; A61M 16/085; A61M 16/10; A61M 2016/0015; A61M 2016/0027;
(Continued)

(56) References Cited

U.S. PATENT DOCUMENTS

| 5,626,131 A | * | 5/1997 | Chua | A61M 16/00 |
| | | | | 128/204.23 |
| 5,632,281 A | * | 5/1997 | Rayburn | A61B 5/0836 |
| | | | | 600/532 |

(Continued)

FOREIGN PATENT DOCUMENTS

| EP | 0728493 A1 | 8/1996 |
| WO | 2006012205 A2 | 2/2006 |

OTHER PUBLICATIONS

D'Mello, J and Butani, M. Capnography, Indian J. Anaesth. 2002; 46(4): 269-278.*

*Primary Examiner* — Tan-Uyen (Jackie) T Ho
*Assistant Examiner* — Joseph D Boecker

(57) ABSTRACT

Pressure support therapy is provided to a subject. The effectiveness of the provided pressure support therapy is determined and/or the therapy is titrated based on determinations of the concentration of one or more gaseous molecular species in gas exhaled by the subject. The determinations of composition of gas exhaled by the subject are obtained from samples with relatively little distortion caused by dilution of expired gases from gases provided to the airway of the subject as part of the pressure support therapy.

18 Claims, 4 Drawing Sheets

(52) U.S. Cl.
CPC ............ *A61M 2016/0021* (2013.01); *A61M 2016/0024* (2013.01); *A61M 2016/0027* (2013.01); *A61M 2205/18* (2013.01); *A61M 2205/3569* (2013.01); *A61M 2205/3592* (2013.01); *A61M 2205/502* (2013.01); *A61M 2205/52* (2013.01); *A61M 2205/582* (2013.01); *A61M 2230/432* (2013.01)

(58) Field of Classification Search
CPC ........ A61M 2016/003; A61M 2205/15; A61M 2205/3331; A61M 2205/3334; A61M 2205/3344; A61M 2205/50; A61M 2206/00; A61M 2206/10; A61M 2230/40; A61M 2230/43; A61M 2230/432

USPC ........... 128/200.24, 200.26, 203.13, 203.14, 128/203.25, 204.18, 204.21–204.23, 128/204.26, 205.27, 205.28, 206.11, 128/206.12, 206.18, 207.14, 207.18; 600/348, 353, 532, 538, 543

See application file for complete search history.

(56) References Cited

U.S. PATENT DOCUMENTS

| | | | |
|---|---|---|---|
| 5,720,277 A | 2/1998 | Olsson | |
| 6,105,575 A | 8/2000 | Estes et al. | |
| 6,581,595 B1* | 6/2003 | Murdock | A61B 5/083 128/204.18 |
| 6,629,527 B1* | 10/2003 | Estes | A61M 16/00 128/202.22 |
| 9,555,205 B2 | 1/2017 | Efrati | |
| 2002/0104536 A1* | 8/2002 | Richey, II | A61M 16/00 128/204.22 |
| 2005/0284484 A1* | 12/2005 | Curti | A61B 5/083 128/207.18 |
| 2006/0042638 A1 | 3/2006 | Niklewski et al. | |
| 2007/0062531 A1* | 3/2007 | Fisher | A61B 5/083 128/204.23 |
| 2007/0068528 A1* | 3/2007 | Bohm | A61B 5/085 128/204.23 |
| 2008/0216833 A1* | 9/2008 | Pujol | A61M 16/00 128/204.21 |
| 2009/0038620 A1 | 2/2009 | Efrati | |
| 2009/0301488 A1* | 12/2009 | Sun | A61M 16/0051 128/204.23 |
| 2012/0145154 A1* | 6/2012 | Baloa Welzien | A61B 5/08 128/204.23 |
| 2012/0234324 A1 | 9/2012 | Orr | |

* cited by examiner

SYSTEM FOR PROVIDING SUPPORT THERAPY WHILE DETERMINING CONCENTRATIONS OF A MOLECULAR GASEOUS EXPIRED BY A SUBJECT RECEIVING PRESSURE SUPPORT THERAPY

BACKGROUND OF THE INVENTION

1. Field of the Invention

The invention relates to determining concentrations of molecular gaseous species exhaled by subjects receiving pressure support therapy.

2. Description of the Related Art

Systems that provide pressure support to a subject are known. Some conventional systems are configured to estimate the concentration of one or more gaseous molecular species in gas expired by the subject to determine the effectiveness of the therapy and/or to titrate the therapy.

In spontaneously breathing, non-intubated subjects, determining the concentration of one or more gaseous molecular species in expired gas is difficult because expired gas is subject to dilution. The dilution may be caused by gas provided by the pressure support system during expiration. Increased leaks to the ambient atmosphere require increased gas to be provided as part of pressure support therapy during expiration causing increased dilution.

SUMMARY OF THE INVENTION

One aspect of the invention relates to a pressure support system comprising a pressure generator, a gas delivery circuit, a first sensor, a second sensor, and a processor. The pressure generator is configured to generate a pressurized flow of breathable gas for delivery to an airway of a subject. The gas delivery circuit is configured to deliver the pressurized flow of breathable gas from the pressure generator to the airway of the subject. The first sensor is configured to generate output signals conveying information related to the breathing phase of the subject. The second sensor is configured to generate output signals conveying information related to the composition of gas at or near the airway of the subject. The one or more processors are configured to execute computer program modules, the computer program modules comprising a control module, a therapy module, and an exhalation composition module. The control module is configured to control the pressure generator to adjust the pressurized flow of breathable gas such that pressure at or near the airway of the subject remains at or above an expiratory pressure level if the output signals generated by the first sensor indicate that the breathing of the subject is in an expiratory phase. The therapy pressure module is configured to set the expiratory pressure level implemented by the control module during expiratory phases of the breathing of the subject, wherein the therapy pressure module is configured such that during most expiratory phases the expiratory pressure level is set at a predetermined baseline expiratory pressure level, and such that intermittently the expiratory pressure level is lowered below the predetermined baseline expiratory pressure level. The exhalation composition module is configured to determine a concentration of a gaseous molecular species in gas exhaled from the lungs of the subject, wherein the exhalation composition module is configured such that the determination of the concentration of the gaseous molecular species in gas exhaled from the lungs of the subject is made based on output signals generated by the second sensor during the intermittent expiratory phases for which the expiratory pressure level is lowered below the predetermined baseline expiratory pressure level.

Another aspect of the invention relates to a method of providing pressure support to a subject. The method comprises generating a pressurized flow of breathable gas for delivery to an airway of a subject; delivering the pressurized flow of breathable gas to the airway of the subject through a flow path; monitoring the breathing phase of the subject; collecting samples indicating a concentration of a gaseous molecular species within the flow path; adjusting the pressurized flow of breathable gas such that pressure at or near the airway of the subject remains at or above an expiratory pressure level if the breathing of the subject is in an expiratory phase; setting the expiratory pressure level implemented during expiratory phases of the breathing of the subject such that during most expiratory phases the expiratory pressure level is set at a predetermined baseline expiratory pressure level, and such that intermittently the expiratory pressure level is lowered below the predetermined baseline expiratory pressure level; and determining a concentration of the gaseous molecular species in gas exhaled from the lungs of the subject based on samples indicating the concentration of the gaseous molecular species within the flow path during the intermittent expiratory phases for which the expiratory pressure level is lowered below the predetermined baseline expiratory pressure level.

Yet another aspect of the invention relates to a system configured to provide pressure support to a subject. In one embodiment, the system comprises means for generating a pressurized flow of breathable gas for delivery to an airway of a subject; means for delivering the pressurized flow of breathable gas to the airway of the subject through a flow path; means for monitoring the breathing phase of the subject; means for collecting samples indicating a concentration of a gaseous molecular species within the flow path; means for adjusting the pressurized flow of breathable gas such that pressure at or near the airway of the subject remains at or above an expiratory pressure level if the breathing of the subject is in an expiratory phase; means for setting the expiratory pressure level implemented during expiratory phases of the breathing of the subject such that during most expiratory phases the expiratory pressure level is set at a predetermined baseline expiratory pressure level, and such that during some non-consecutive expiratory phases the expiratory pressure level is lowered below the predetermined baseline expiratory pressure level; and means for determining a concentration of the gaseous molecular species in gas exhaled from the lungs of the subject based on samples indicating the concentration of the gaseous molecular species within the flow path during the non-consecutive expiratory phases for which the expiratory pressure level is lowered below the predetermined baseline expiratory pressure level.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the inven-

DETAILED DESCRIPTION OF THE EXEMPLARY EMBODIMENTS

Figure 1:
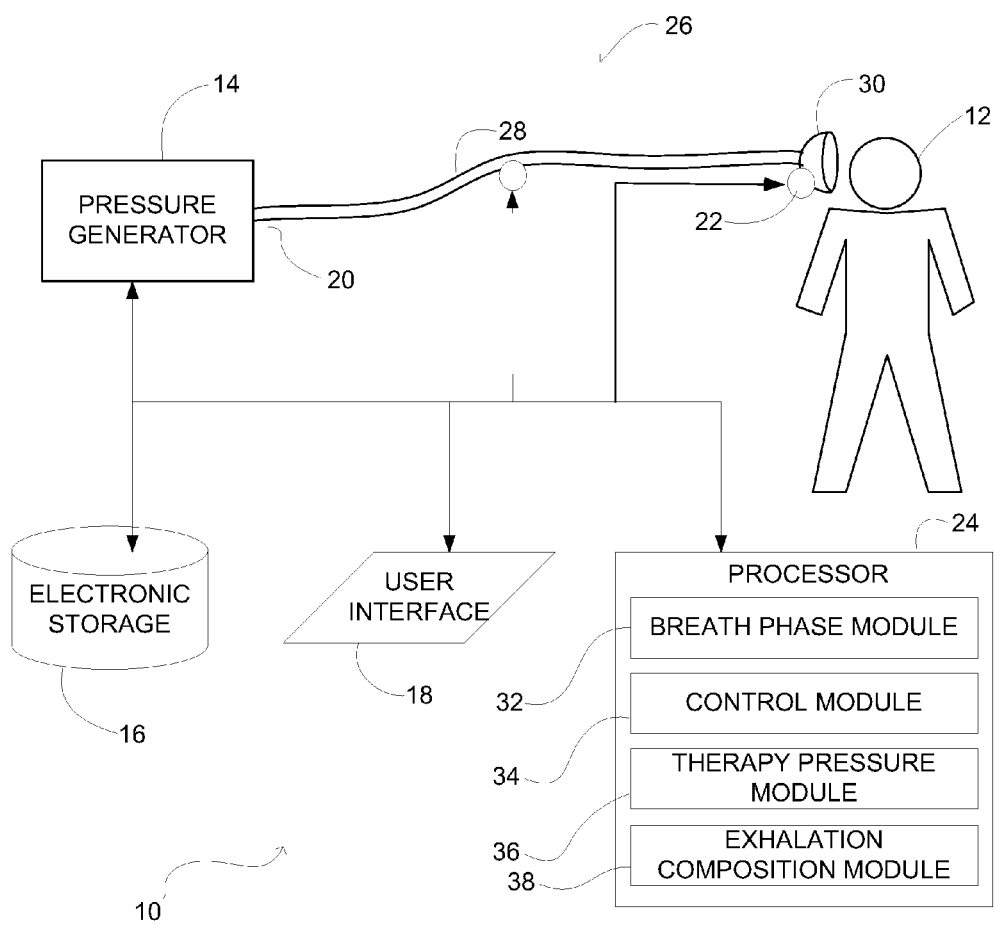
FIG. 1 illustrates a system configured to provide pressure support therapy to a subject, according to one or more embodiments of the invention.

FIG. 1 illustrates a system 10 configured to provide pressure support therapy to a subject 12. The system 10 is also configured to determine the effectiveness of the provided pressure support therapy. This determination includes determining the concentration of one or more gaseous molecular species in gas exhaled by subject 12. For example, a determination of the concentration of carbon dioxide ($CO_2$) in gas exhaled by subject 12 (e.g., end-tidal $CO_2$ concentration) may be made to enable a determination of the effectiveness of the provided pressure support therapy. The system 10 is configured to provide determinations of composition of gas exhaled by subject 12 with relatively low levels of dilution caused by gases from other source (e.g., ambient atmosphere, the pressure support therapy, etc.). In one embodiment, system 10 includes one or more of a pressure generator 14, electronic storage 16, a user interface 18, a first sensor 20, a second sensor 22, a processor 24, and/or other components.

In one embodiment, pressure generator 14 is configured to generate a pressurized flow of breathable gas for delivery to the airway of subject 12. The pressure generator 14 may control one or more parameters of the pressurized flow of breathable gas (e.g., flow rate, pressure, volume, humidity, temperature, gas composition, etc.) for therapeutic purposes, or for other purposes. By way of non-limiting example, pressure generator 14 may be configured to control the flow rate and/or pressure of the pressurized flow of breathable gas to provide pressure support to the airway of subject 12. The pressure generator 14 may include a ventilator, a positive airway pressure generator such as, for example, the device described in U.S. Pat. No. 6,105,575, hereby incorporated by reference in its entirety, and/or other pressure generation devices. The pressure support provided by subject 14 via the pressurized flow of breathable gas may include, for example, non-invasive ventilation, positive airway pressure support, bi-level support, BiPAP®, and/or other types of pressure support therapy.

The pressurized flow of breathable gas is delivered to the airway of subject 12 via a gas delivery circuit 26. Gas delivery circuit 26 is configured to communicate the pressurized flow of breathable gas generated by pressure generator 14 to the airway of subject 12. As such, gas delivery circuit 26 includes a conduit 28 and an interface appliance 30. Conduit 28 conveys the pressurized flow of breathable gas to interface appliance 30, and interface appliance 30 delivers the pressurized flow of breathable gas to the airway of subject 12. Some examples of interface appliance 30 may include, for example, a nasal cannula, a nasal mask, a nasal/oral mask, a full face mask, a total face mask, and/or other interface appliances that communicate a flow of gas with an airway of a subject. The present invention is not limited to these examples, and contemplates delivery of the pressurized flow of breathable gas to subject 12 using any subject interface.

Although gas delivery circuit 26 is illustrated in FIG. 1 as a single-limbed circuit for the delivery of the pressurized flow of breathable gas to the airway of subject 12, this is not intended to be limiting. The scope of this disclosure includes double-limbed circuits having a first limb configured to both provide the pressurized flow of breathable gas to the airway of subject 12, and a second limb configured to selectively exhaust gas from gas delivery circuit 26 (e.g., to exhaust exhaled gases). Further, the illustration of interface appliance 30 as a single device is not intended to be limiting. It will be appreciated that interface appliance 30 may include at least two separate interface appliances. For example, a first interface appliance (e.g., a full face mask, a total face mask, etc.) may be configured to provide the pressurized flow of breathable gas to subject 12 while a second interface appliance (e.g., a nasal cannula, etc.) is configured to receive gas from the airway of the subject 12 so that parameters of the gas received from the airway of subject 12 can be measured (e.g., composition).

In one embodiment, electronic storage 16 comprises electronic storage media that electronically stores information. The electronic storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 24, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., generator 14, user interface 18, processor 24, etc.).

User interface 18 is configured to provide an interface between system 10 and subject 12 through which subject 12 may provide information to and receive information from system 10. This enables data, cues, results, and/or instructions and any other communicable items, collectively referred to as "information," to be communicated between the subject 12 and one or more of generator 14, electronic storage 16, and/or processor 24. Examples of interface devices suitable for inclusion in user interface 18 include a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 18 includes a plurality of separate interfaces. In one embodiment, user interface 18 includes at least one interface that is provided integrally with generator 14.

It is to be understood that other communication techniques, either hard-wired or wireless, are also contemplated by the present invention as user interface 18. For example, the present invention contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present invention as user interface 18.

The first sensor 20 is configured to generate output signals conveying information related to one or more parameters of the pressurized flow of breathable gas. The one or more parameters may include, for example, one or more of a flow rate, a volume, a pressure, humidity, temperature, acceleration, velocity, acoustics, changes in a parameter indicative of respiration, and/or other gas parameters. As such, the output signals generated by first sensor 20 convey information related to the breathing phase of subject 12. The first sensor 20 may include one or more sensors that measure such parameters directly (e.g., through fluid communication with the pressurized flow of breathable gas at pressure generator 14 or in gas delivery circuit 26). The first sensor 20 may include one or more sensors that generate output signals related to one or more parameters of the pressurized flow of breathable gas indirectly. For example, first sensor 20 may include one or more sensors configured to generate an output based on an operating parameter of pressure generator 14 (e.g., a valve driver or motor current, voltage, rotational velocity, and/or other operating parameters), and/or other sensors.

Although first sensor 20 is illustrated as a single sensor at a single location within gas delivery circuit 26, this is not intended to be limiting. The first sensor 20 may include a plurality of sensors which may be located proximately or separately with respect to each other. Sensors providing the functionality attributed herein to first sensor 20 may be disposed in any of a plurality of locations, such as for example, within pressure generator 14, within (or in communication with) conduit 28, within (or in communication with) interface appliance 30, and/or other locations.

The second sensor 22 is configured to generate output signals conveying information related to the composition of gas at or near the airway of subject 12. In one embodiment, the output signals generated by second sensor 22 convey information related to the concentration of $CO_2$, and/or other gases, in contact or communication with second sensor 22. As was discussed above, the output signals generated by second sensor 22 may be used to determine end-tidal $CO_2$ for subject 12. To determine end-tidal $CO_2$, detecting $CO_2$ concentration in a sample of alveolar gas will provide enhanced accuracy. In therapeutic settings in which interface appliance 30 provides for sealed communication with the airway of subject 12 (e.g., an endo-tracheal tube), obtaining such a sample in a sampling chamber accessible to second sensor 22 is easy, as all of the gas expired from the lungs of subject 12 must flow out of interface appliance 30. However, in non-invasive pressure support therapies, obtaining an alveolar gas sample may be more difficult because as gas exits the airway of subject 12 it can be actively diluted by air supplied by pressure generator 14 in an effort to maintain pressure in the presence of leaks to ambient air.

In order to somewhat reduce dilution, interface appliance 30 may include two separate interface appliances, one to deliver the pressurized flow of breathable gas, and one to acquire samples of gas exhaled by subject 12. For example, as was discussed above, interface appliance 30 may include a mask configured to deliver the pressurized flow of breathable gas, and a nasal cannula underneath the mask that is installed in the nares of subject 12 to collect gas exhaled by subject 12.

Processor 24 is configured to provide information processing capabilities in system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may include a plurality of processing units. These processing units may be physically located within the same device (e.g., pressure generator 14), or processor 24 may represent processing functionality of a plurality of devices operating in coordination.

As is shown in FIG. 1, processor 24 may be configured to execute one or more computer program modules. The one or more computer program modules may include one or more of a breath phase module 32, a control module 34, a therapy pressure module 36, a exhalation composition module 38, and/or other modules. Processor 24 may be configured to execute modules 32, 34, 36, and/or 38 by software; hardware; firmware; some combination of software, hardware, and/or firmware; and/or other mechanisms for configuring processing capabilities on processor 24.

It should be appreciated that although modules 32, 34, 36, and 38 are illustrated in FIG. 1 as being co-located within a single processing unit, in implementations in which processor 24 includes multiple processing units, one or more of modules 32, 34, 36, and/or 38 may be located remotely from the other modules. The description of the functionality provided by the different modules 32, 34, 36, and/or 38 described below is for illustrative purposes, and is not intended to be limiting, as any of modules 32, 34, 36, and/or 38 may provide more or less functionality than is described. For example, one or more of modules 32, 34, 36, and/or 38 may be eliminated, and some or all of its functionality may be provided by other ones of modules 32, 34, 36, and/or 38. As another example, processor 24 may be configured to execute one or more additional modules that may perform some or all of the functionality attributed below to one of modules 32, 34, 36, and/or 38.

The breath phase module 32 is configured to determine the phase of respiration of subject 12. The breath phase module 32 determines the phase of respiration based on the output signals generated by first sensor 20. For example, fluctuations in flow rate, pressure and/or other parameters indicated in the output signals generated by first sensor 20 may be implemented by breath phase module 32 to determine the phase of respiration of subject 12. Determining the phase of respiration includes determining whether the breathing of subject 12 is in the inspiratory phase or the expiratory phase. In one embodiment, breath phase module 32 is configured to determine more than breathing transitions from inspiratory phase to expiratory phase and vice versa. For example, may be configured to determine when the breathing of subject 12 reaches one or more points in the inspiratory phase and/or expiratory phase. In one embodiment, processor 24 includes one or more processors within a first device that includes pressure generator 14, and one or more processors within a second device configured to determine information related to the composition of gas exhaled by subject 12. In this embodiment, breath phase module 32 may include one or more modules executed on the device configured to determine information related to the composition of gas exhaled by subject 12. The one or more modules of the second may determine respiration phase based on determinations of respiration phase made by the first device in order to adjust the pressurized flow of breathable gas according to the therapy regime.

The control module 34 is configured to control pressure generator 14 to adjust the pressurized flow of breathable gas such that pressure at or near the airway of subject 12 follows a therapy regime. The therapy regime may dictate a target pressure at or near the airway of subject 12 as a function of the phase of the breathing of subject 12. As breath phase module 32 determines the phase of respiration of subject 12, control module 34 implements this determination to determine the target pressure at or near the airway of subject 12 dictated by the therapy regime. The control module 34 then controls pressure generator 14 to adjust the pressurized flow of breathable gas to achieve and/or maintain this target pressure.

By way of non-limiting example, in one embodiment, the therapy regime specifies an expiratory pressure level and an inspiratory pressure level. The inspiratory pressure level is substantially higher than the expiratory pressure level. During the inspiratory phase of respiration, control module 34 controls pressure generator 14 to adjust the pressurized flow of breathable gas such that pressure at or near the airway of subject 12 is adjusted toward the inspiratory pressure level. Maintenance of relatively high pressure at or near the airway of subject 12 during the inspiratory phase of respiration makes it easier for subject 12 to inhale. During the expiratory phase of respiration, control module 34 controls pressure generator 14 to adjust the pressurized flow of breathable gas such that pressure at or near the airway of subject 12 is reduced to less than inspiratory phase pressure so that subject 12 does not have to exhale "against" too much pressure. However, even during the expiratory phase of respiration, control module 34 does not permit pressure at or near the airway of subject 12 to fall below the expiratory pressure level. The expiratory pressure level may be set to a level that will facilitate exhalation by subject 12, and yet safeguards against alveolar deterioration and prevent airway closure.

The therapy pressure module 36 is configured to adjust the pressures dictated by the therapy regime. These adjustments include adjusting the pressures dictated by the therapy regime to facilitate determinations of end-tidal $CO_2$.

During expiration, control module 34 causes pressure generator 14 to adjust the pressurized flow of breathable gas to maintain pressure at or near the airway of subject 12 at or above the expiratory pressure level. Typically, the expiratory pressure level is reached relatively soon after respiration changes from the inspiratory to expiratory phase, which results in an increase in flow rate of the pressurized flow of breathable gas to maintain pressure at or near the airway of subject 12. As was discussed above, obtaining accurate end-tidal $CO_2$ requires obtaining sufficiently pure expired gas for second sensor 22 to measure $CO_2$ composition with relatively low amounts of dilution. The increase in flow rate of the pressurized flow of breathable gas during expiration to maintain the expiratory pressure level is a primary source of dilution of gas exhaled by subject 12, and makes obtaining sufficiently pure expired gas for second sensor 22 to measure $CO_2$ composition challenging.

Figure 2:
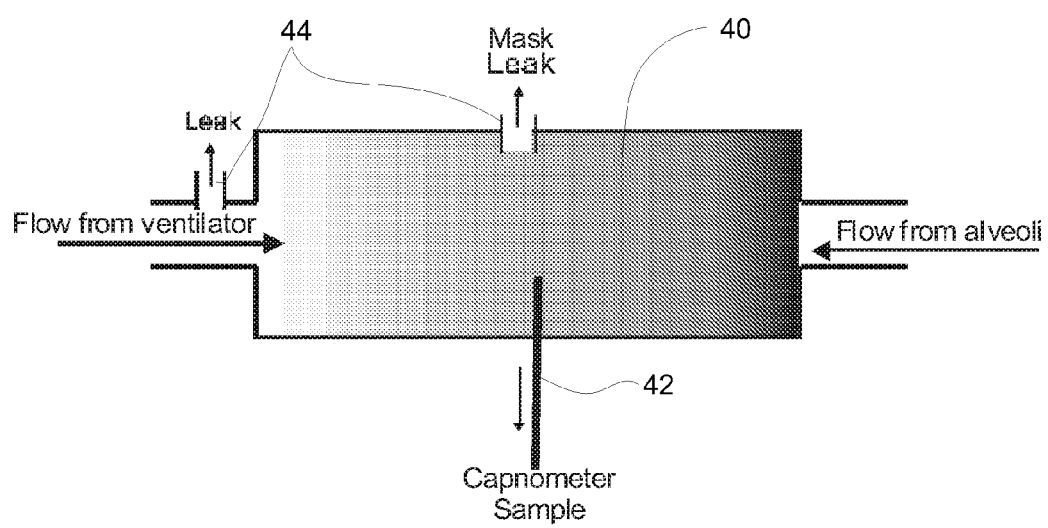
FIG. 2 illustrates a schematic model of the sampling of gas exhaled by a subject, in accordance with one or more embodiments of the invention.

By way of illustration, FIG. 2 is a schematic model of the sampling of gas exhaled by a subject. The shaded box represents a volume 40 defined by an interface appliance similar to or the same as interface appliance 30 (shown in FIG. 1 and described herein) and the airway of the subject. The sample of gas used by a composition sensor that is the same as or similar to second sensor 22 (shown in FIG. 1 and described herein) is labeled as element 42. The dark shading represents gas that is purely expired from the alveoli of the lungs, and therefore contains an alveolar $CO_2$ concentration. The light shading represents other gases that function to dilute the expired gas. The diluting gases comprise primarily the pressurized flow of breathable gas provided from a pressure generator that is the same as or similar to pressure generator 14 (shown in FIG. 1 and described herein). As was discussed above, leaks 44 between the volume 42 and atmosphere require an increased amount of gas to be delivered in pressurized flow of breathable gas to maintain pressure, thereby increasing dilution.

Returning to FIG. 1, therapy pressure module 36 is configured to sporadically adjust the expiratory pressure level of the therapy regime to reduce dilution of expired gas sampled by second sensor 22. This results in the expiratory pressure level for most expiratory phases being set at a baseline expiratory pressure level that facilitates expiration while providing the benefits of airway and/or lung pressure support to subject 12. However, during some expiratory phases, therapy pressure module 36 lowers the expiratory pressure implemented by control module 34 to reduce dilution of expired gases during these expiratory phases.

Figure 3:
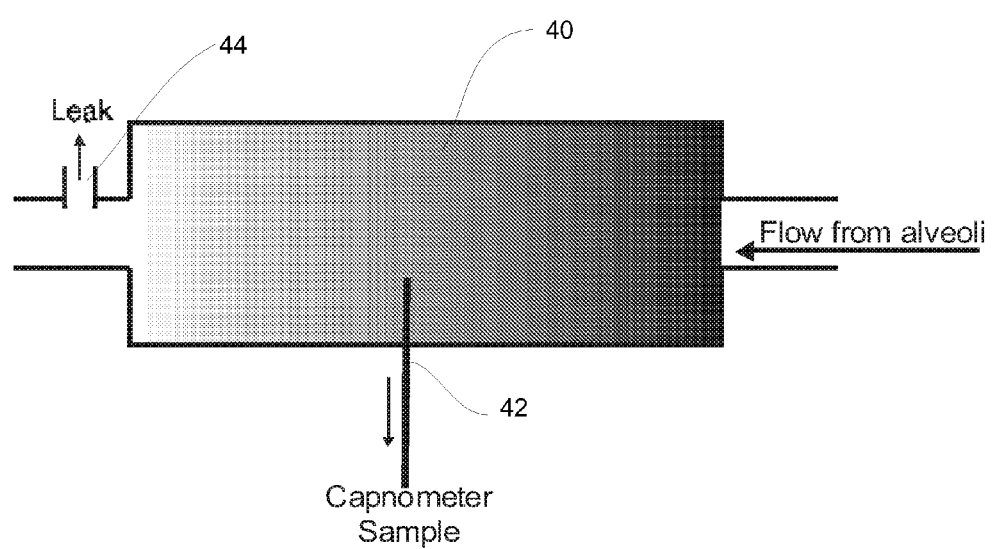
FIG. 3 illustrates a schematic model of the sampling of gas exhaled by a subject, according to one or more embodiments of the invention.

By way of illustration, FIG. 3 shows volume 40 (also depicted in FIG. 2 and discussed above) during an expiratory phase in which the flow rate of the pressurized flow of breathable gas is reduced, if not ceased altogether. As can be seen in FIG. 3, this tends to decrease the dilution of expired gases, thereby enabling a more accurate determination of end-tidal $CO_2$. In addition to reducing dilution of expired gas, the reduction in flow of the pressurized flow of breathable gas may further enable the subject to exhale more completely, thereby increasing the volume of expired gas introduced into volume 40 and further decreasing dilution from other gases.

Returning to FIG. 1, as has been discussed above, the reduction of the expiratory pressure level uniformly across respiration may reduce the benefits of the pressure support provided by system 10. However, by intermittently lowering the expiratory pressure level (e.g., during temporally spaced out, non-consecutive breaths) therapy pressure module 36 enables samples of less diluted expiratory gas to be taken without detrimentally impacting the therapy received by subject 12.

Figure 4:
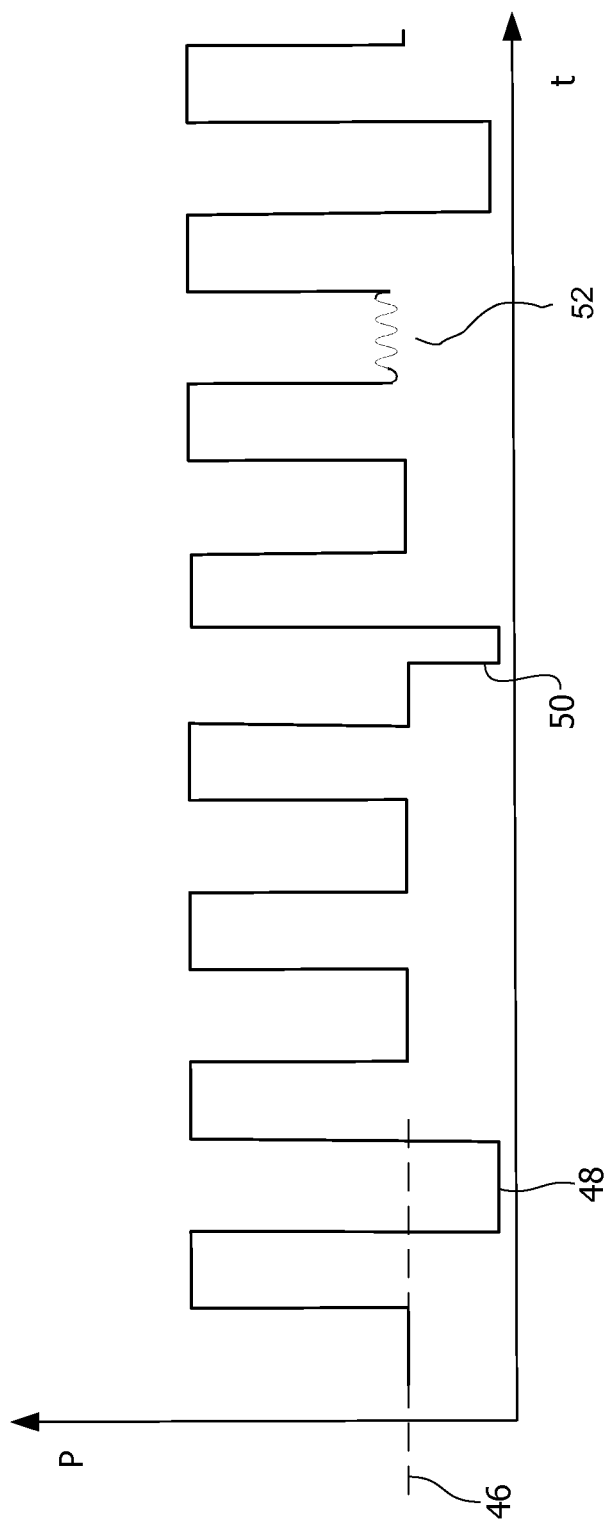
FIG. 4 a plot of pressure versus time dictated by a therapy regime, in accordance with one or more embodiments of the invention.

FIG. 4 illustrates a plot of pressure versus time dictated by a therapy regime. As can be seen in FIG. 4, during inspiratory phases, pressure dictated by the therapy regime is at an inspiratory pressure level. During most expiratory phases, pressure dictated by the therapy regime is at a baseline expiratory pressure level 46. However, intermittently at some expiratory phases, the expiratory pressure level is reduced to permit sampling of end-tidal $CO_2$ with reduced dilution. This reduction in expiratory pressure level may be applied throughout a given expiratory phase, such as is shown in expiratory phase 48, or may be applied during only a portion of the given expiratory phase, such as is shown in expiratory phase 50.

Returning to FIG. 1, the determination of which expiratory phases should be provided with a reduced expiratory pressure level by therapy pressure module 36 may be made with a periodicity. This periodicity may be quantified by a number of breaths (e.g., expiratory pressure level is reduced every X breaths), and/or by passage of time (e.g., expiratory level is reduced every X seconds). This periodicity may be a configurable setting that can be selectively configured by a user via user interface 18. In one embodiment, the determination of which expiratory phases should be provided with a reduced expiratory pressure level by therapy pressure module 36 may be made stochastically or even randomly (or pseudo-randomly) by therapy pressure module 36. In this embodiment, some control over the relative frequency with which a reduced expiratory pressure level is provided may be provided to a user via user interface 18. The amount of reduction below the baseline expiratory pressure may be a configurable setting that can be selectively configured by a user via user interface 18.

In one embodiment, therapy pressure module 36 is configured that for breaths during which the expiratory pressure level is not set below the baseline expiratory pressure level there is still some variance between the expiratory pressure level. For example, therapy pressure module 36 may be configured to vary the expiratory pressure level in a periodic sinusoidal fashion as in an expiratory phase 52 shown in FIG. 4. The range of expiratory pressures over which the sinusoid travels may be configured such that the expiratory pressure level falls below the baseline expiratory pressure level only at or near the minima of the sinusoid.

The exhalation composition module 38 is configured to determine a concentration of a gaseous molecular species in gas exhaled from the lungs of subject 12 based on output signals generated by second sensor 22. In one embodiment, this includes a determination of end-tidal $CO_2$. The determination of the concentration of the gaseous molecular species is made by exhalation composition module 38 using only output signals generated during expiratory phases in which therapy pressure module 36 has set the expiratory pressure level below the baseline expiratory pressure level. This ensures that the determination is based on samples of the concentration of the gaseous molecular species that are less distorted by dilution than samples of the concentration of the gaseous molecular species taken during expirations in which the expiratory pressure level is at or above the baseline expiratory pressure level.

From determinations of the gaseous molecular species in gas exhaled from the lungs of subject 12 made by exhalation composition module 38, the effectiveness of the pressure support provided by system 10 may be determined. This determination may be made by processor 24, and may be based on determinations of other respiratory parameters measured and/or estimated from, for example, output signals generated by first sensor 20. Determinations of the effectiveness of the pressure support and/or the determinations of the gaseous molecular species in gas exhaled from the lungs of subject 12 may be implemented by processor 24 to titrate the pressure support. For example, the therapy regime implemented by control module 34 to determine control of pressure generator 14 may be adjusted based on such determinations to enhance the therapeutic benefit of the pressure support to subject 12.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pressure support system comprising:
   a gas delivery circuit including
       a pressure generator configured to generate a pressurized flow of breathable gas,
       an interface for connecting to an airway of a subject,
       a conduit connecting the pressure generator and the interface and configured to deliver the pressurized flow of breathable gas to the airway of the subject,
       a first sensor connected to the delivery circuit and configured to identify expiratory and inspiratory phases of breathing of the subject, and
       a second sensor connected to the interface and configured to sense composition of gas at or near the airway of the subject; and
   one or more processors configured to during the expiratory phases:
       control the pressure generator to adjust the pressurized flow of breathable gas such that pressure at or near the airway of the subject remains at or above an expiratory pressure level,
       set the expiratory pressure level at a predetermined baseline except during some of the expiratory phases when the expiratory pressure level is set below the predetermined baseline, and
       determine a concentration of a gaseous molecular species in gas exhaled from the lungs of the subject based on the sensed composition of gas only during the expiratory phases for which the expiratory pressure level is lowered below the predetermined baseline;
       wherein the expiratory phases for which the expiratory pressure level is lowered below the predetermined baseline occur during non-consecutive breaths that are spaced apart in time.

2. The pressure support system of claim 1, wherein the gaseous molecular species is carbon dioxide.

3. The pressure support system of claim 1, wherein the one or more processors are further configured during the inspiratory phase to control the pressure generator to adjust the pressurized flow of breathable gas to increase pressure at or near the airway of the subject to an inspiratory pressure level, wherein the inspiratory pressure level is substantially higher than the expiratory pressure level.

4. The pressure support system of claim 1, wherein the expiratory pressure level is set below the predetermined baseline with a periodicity quantified as either a predetermined number of breaths, or a predetermined period of time.

5. The pressure support system of claim 4, wherein the expiratory pressure level is determined according to a sinusoid that dictates the magnitude of the expiratory pressure level.

6. The pressure support system of claim 4, wherein the predetermined number of breaths is greater than one breath.

7. The pressure support system of claim 4, wherein the predetermined period of time is a time period longer than one breath.

8. A method of providing pressure support to a subject, the method comprising:
   generating a pressurized flow of breathable gas;
   delivering the pressurized flow of breathable gas to an airway of the subject through a flow path;

monitoring breathing of the subject to identify expiratory and inspiratory phases;

collecting samples indicating a concentration of a gaseous molecular species within the flow path;

during the expiratory phases adjusting the pressurized flow of breathable gas such that pressure at or near the airway of the subject remains at or above an expiratory pressure level;

setting the expiratory pressure level at a predetermined baseline except during some of the expiratory phases, setting the expiratory pressure level below the predetermined baseline; and determining a concentration of the gaseous molecular species in gas exhaled from the lungs of the subject based on samples indicating the concentration of the gaseous molecular species within the flow path only during the expiratory phases for which the expiratory pressure level is lowered below the predetermined baseline, wherein the expiratory phases for which the expiratory pressure level is lowered below the predetermined baseline occur during non-consecutive breaths that are spaced apart in time.

9. The method of claim 8, wherein the gaseous molecular species is carbon dioxide.

10. The method of claim 8, further comprising during the inspiratory phase adjusting the pressurized flow of breathable gas to increase pressure at or near the airway of the subject to an inspiratory pressure level, wherein the inspiratory pressure level is substantially higher than the expiratory pressure level.

11. The method of claim 8, the expiratory pressure level is set below the predetermined baseline with a periodicity quantified as either a predetermined number of breaths, or a predetermined period of time.

12. The method of claim 11, wherein the expiratory pressure level is determined according to a sinusoid that dictates the magnitude of the expiratory pressure level.

13. The method of claim 11, wherein the predetermined number of breaths is greater than one breath.

14. A system configured to provide pressure support to a subject, the system comprising:

a circuit including
a generator for generating a pressurized flow of breathable gas,
a flow path for connecting to an airway of the subject,
a conduit connecting the generator and the flow path for delivering the pressurized flow of breathable gas to the airway of the subject through the flow path,
one or more first sensors connected to the circuit for monitoring breathing of the subject to identify expiratory and inspiratory phases, and
one or more second sensors connected to the flow path for collecting samples indicating a concentration of a gaseous molecular species within the flow path, wherein the one or more second sensors are located downstream of the generator when considering the subject as downstream of the generator; and at least one processor for during the expiratory phases:
adjusting the pressurized flow of breathable gas such that pressure at or near the airway of the subject remains at or above an expiratory pressure level,
setting the expiratory pressure level such that
during the expiratory phases the expiratory pressure level is set at a predetermined baseline and
during some non-consecutive expiratory phases the expiratory pressure level is lowered below the predetermined baseline; and
determining a concentration of the gaseous molecular species in gas exhaled from the lungs of the subject based on samples indicating the concentration of the gaseous molecular species within the flow path only during the non-consecutive expiratory phases for which the expiratory pressure level is lowered below the predetermined baseline.

15. The system of claim 14, wherein the gaseous molecular species is carbon dioxide.

16. The system of claim 14, wherein the at least one processor further during the inspiratory phase adjusts the pressurized flow of breathable gas to increase pressure at or near the airway of the subject to an inspiratory pressure level, wherein the inspiratory pressure level is substantially higher than the expiratory pressure level.

17. The system of claim 14, wherein the expiratory pressure level is set below the predetermined baseline with a periodicity quantified as either a predetermined number of breaths, or a predetermined period of time.

18. The system of claim 17, wherein the expiratory pressure level is determined according to a sinusoid that dictates the magnitude of the expiratory pressure level.

* * * * *